US00PP37134P2

(12) United States Plant Patent
Van Haaster

(10) Patent No.: US PP37,134 P2
(45) Date of Patent: Dec. 9, 2025

(54) ***DAHLIA* PLANT NAMED 'DDAHCHPRPL'**

(50) Latin Name: ***Dahlia* hybrid**
Varietal Denomination: DDAHCHPRPL

(71) Applicant: Ans Van Haaster, Hillegom (NL)

(72) Inventor: Ans Van Haaster, Hillegom (NL)

( * ) Notice: Subject to any disclaimer, the term of this patent is extended or adjusted under 35 U.S.C. 154(b) by 0 days.

(21) Appl. No.: 19/025,753

(22) Filed: Jan. 16, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Shubo Zhou
*Assistant Examiner* — Zachariah Allan Kay

(57) ABSTRACT

A new and distinct cultivar of *Dahlia* plant named 'DDAHCHPRPL' is disclosed, characterized by double flowers with dark purple centers and light purple margins. Plants have upright habits and dark green foliage. The new variety is a *Dahlia*, typically produced as an ornamental plant.

2 Drawing Sheets

Figure 1:
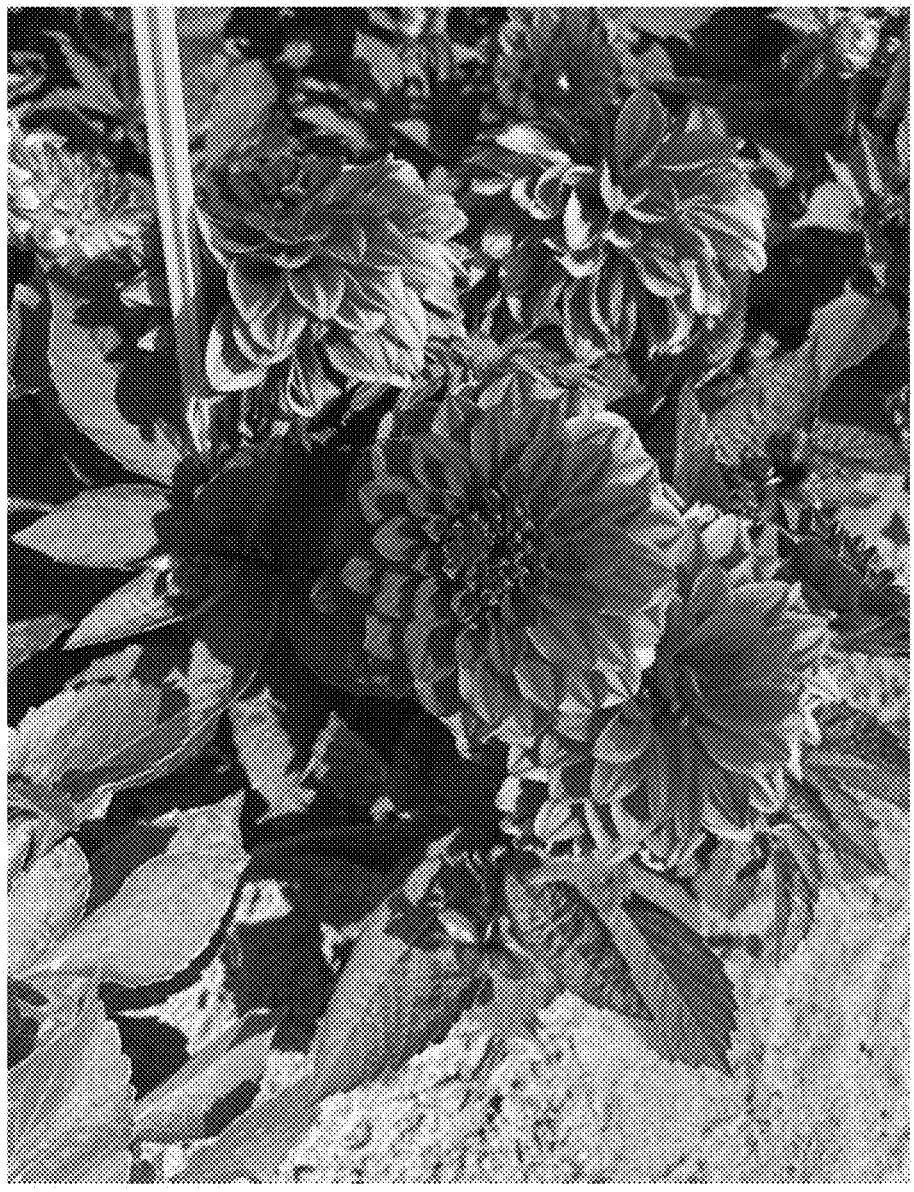

Latin name of the genus and species: *Dahlia* hybrid.
Variety denomination: 'DDAHCHPRPL'.

BACKGROUND OF THE INVENTION

The new *Dahlia* cultivar is a product of a planned breeding program conducted by the inventor, Ans van Haaster in Hillegom, the Netherlands. The objective of the breeding program was to produce useful new *Dahlia* varieties for ornamental horticultural production. The crossing resulting in this new variety was made in August 2020.

The seed parent is the unpatented variety *Dahlia* 'Hypnotica Pink'. The pollen parent is the unpatented variety *Dahlia* 'Hypnotica Lavender'. The new variety was discovered in August 2021 by the inventor in a group of seedlings in Hillegom, the Netherlands. Asexual propagation of *Dahlia* was performed by vegetative cuttings in September 2021, at the same location in Hillegom, the Netherlands. After selection of the new variety, extensive confidential testing has been performed to determine and define the desirable characteristics of the new variety.

SUMMARY OF THE INVENTION

The cultivar 'DDAHCHPRPL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDAHCHPRPL'. These characteristics in combination distinguish 'DDAHCHPRPL' as a new and distinct *Dahlia* cultivar:

1. Double flowers with darker purple centers and lighter purple margins.
2. Flower stems are short and close to the foliage.

PARENT COMPARISONS

Plants of 'DDAHCHPRPL' are similar in some horticultural characteristics to the seed parent. The new variety, however, differs in the following:

1. Flower color of the new variety is purple, while the flower color of the seed parent is pink.
2. Leaves of the new variety are smaller than leaves of the seed parent.
3. Plants of the new variety are not as vigorous as plants of the seed parent.

Plants of 'DDAHCHPRPL' are similar in some horticultural characteristics to the pollen parent. The new variety, however, differs in the following:

1. Flower color of the new variety is a darker purple than the flower color of the pollen parent.
2. Plants of the new variety are not as tall as plants of the pollen parent.
3. The flower gradient color in Hypnotica Lavender is greater than in 'DDAHCHPRPL'.
4. Leaves of the new variety are smaller than leaves of the pollen parent.
5. Leaves of the new variety are darker green than leaves of the pollen parent.

COMMERCIAL COMPARISONS

Plants of 'DDAHCHPRPL' are similar in some horticultural characteristics to the variety *Dahlia* 'Dahlietta Emily', unpatented. The new variety, however, differs in the following:

1. Plants of the new variety are less compact than plants of this comparator.
2. Flower color of the new variety is a darker purple than the flower color of this comparator.
3. Flowers of the new variety are larger than flowers of this comparator.

Plants of 'DDAHCHPRPL' are similar in some horticultural characteristics to the variety *Dahlia* "Labella Grande Purple Improved", unpatented. The new variety, however, differs in the following:

1. Flower stems of the new variety are shorter than the flower stems of this comparator.
2. Flowers of the new variety have more petals than flowers of this comparator.

3. Flower color of the new variety is lighter purple than the flower color of this comparator.

BRIEF DESCRIPTION OF THE PHOTOGRAPHS

The accompanying photograph in FIG. 1 illustrates in full color a typical plant of 'DDAHCHPRPL' 80 days from planting, grown outdoors in a trial field.

Figure 2:
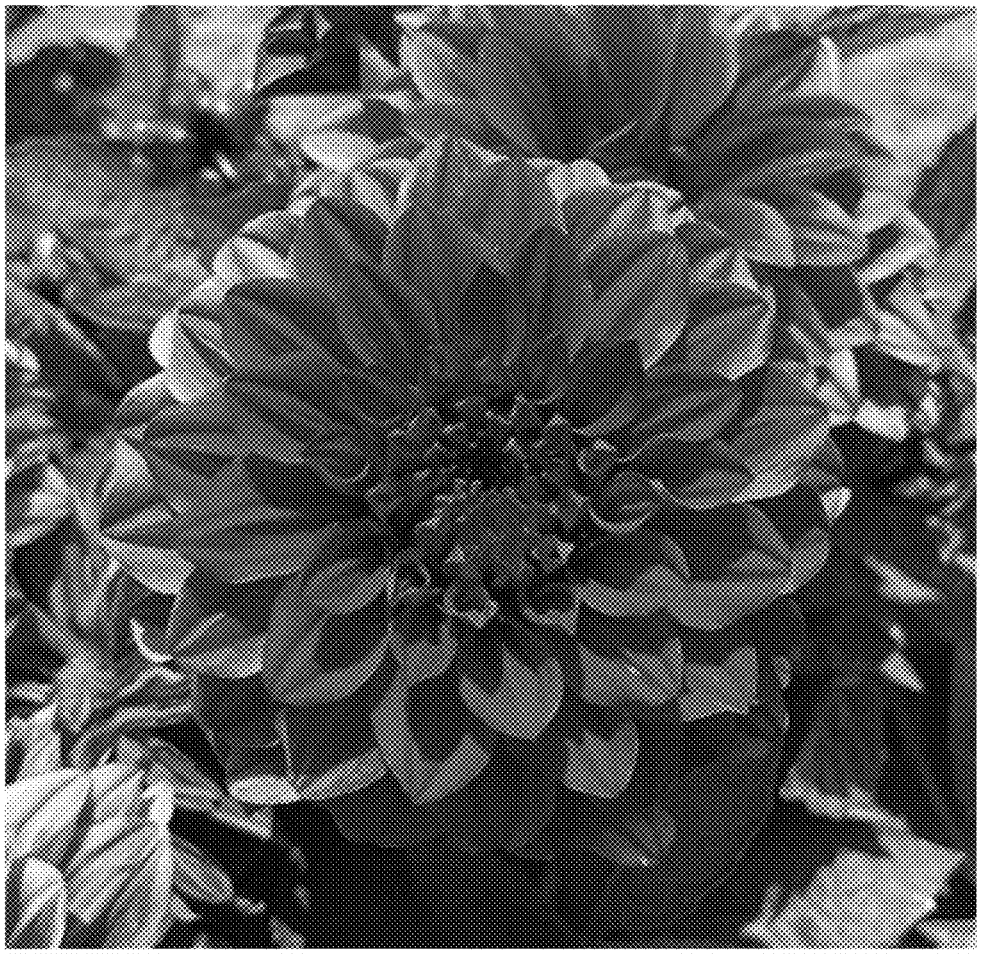

FIG. 2 illustrates a closer view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DDAHCHPRPL' plants grown in a plastic tunnel in Hillegom, the Netherlands, under natural lighting. Measurements were taken August 2024. The growing temperature ranged from approximately 15° C. to 32° C. during the days, 8° C. to 20° C. during the nights. Measurements and numerical values represent averages of typical plant types.

Botanical classification: *Dahlia* hybrid 'DDAHCHPRPL'.

PROPAGATION

Propagation method: Vegetative cuttings.
Time to initiate rooting: 8 to 15 days in summer; 12 to 17 days in winter.
Root description: Fibrous and relatively shallow in the early stages of development. Roots grow more complex as the plant matures.
Tuber description: Skin firm and relatively thin, colored light brown. Inner flesh moist and firm, colored white. Colors not accurately measured with R.H.S. chart.

PLANT

Age of plant described: 80 days from a rooted cutting.
Growth habit: Upright.
Pot size of plant described: 13 cm.
Height: 29 cm.
Plant spread: 35 cm.
Branching characteristics:
Length of lateral branches: 10 cm.
Diameter of lateral branches: 4 to 7 mm.
Quantity of lateral branches: 8 per main stem.
Characteristics of primary lateral branches:
- *Diameter.*—0.7 cm.
- *Color.*—RHS Yellow-Green 144B.
- *Texture.*—Smooth.

Internode length: 5 cm.

FOLIAGE

Leaf:
- *Arrangement.*—Compound.

Leaflets:
- *Shape.*—Triangle.
- *Quantity.*—Approximately 3 per branch.
- *Average overall length.*—15 cm.
- *Average overall width.*—11 cm.

Individual leaf blades:
- *Shape.*—Broad elliptic.
- *Apex.*—Tapered to a point.
- *Base.*—Rounded, sometimes slightly cordate (heart-shaped).
- *Margin.*—Serrate, jagged.
- *Texture.*—Smooth.
- *Pubescence.*—None.
- *Color.*—Young foliage upper side: RHS Green 136B. Young foliage under side: RHS Green 139C. Mature foliage upper side: RHS Green 136A. Mature foliage under side: RHS Green 136C.
- *Venation.*—Pattern: Reticulate-central main vein runs through the length of the leaf, with smaller lateral veins branching off from it in a feather-like pattern. Color, upper side: RHS Yellow-Green 144B. Color, under side: RHS Green 136C.

Petiole:
- *Length.*—2.2 cm.
- *Diameter.*—0.2 cm.
- *Color.*—RHS Green 139C.
- *Texture.*—Smooth.

Stipule:
- *Length.*—4 cm.
- *Diameter.*—0.5 cm.
- *Color.*—RHS Green 139C.
- *Texture.*—Smooth.

FLOWER

Natural flowering season: Summer to autumn.
Days to flowering from rooted cutting: 55 days.
Inflorescence and flower type and habit: Decorative.
Rate of flower opening: 6 to 11 days from bud to fully opened flower.
Flower longevity on plant: 22 days.
Persistent or self-cleaning: Persistent.

Bud:
- *Shape.*—Round.
- *Length.*—2 cm.
- *Diameter.*—2.2 cm.
- *Color.*—RHS Red-Purple 71A.

Flower size:
- *Diameter.*—11 cm.
- *Depth.*—2.5 cm.

Petals:
- *Arrangement.*—Double flower, radial symmetry.
- *Length.*—4.8 cm.
- *Width.*—2.6 cm.
- *Quantity.*—About 140.
- *Texture.*—Smooth.
- *Apex.*—Round.
- *Base.*—Pointed.
- *Shape.*—Oval.
- *Margin.*—Straight, smooth.
- *Color.*—When Opening, Upper Surface: RHS Red-Purple 71A margin 70C. When Opening, Lower Surface: RHS Red-Purple 71B. Fully Opened, Upper Surface: RHS Red-Purple 71A margin 70D. Fully Opened, Lower Surface RHS Red-Purple 71B.

Sepals:
- *Quantity per flower.*—7.
- *Shape.*—Oval.

*Length*.—1.5 cm.
*Width*.—1 cm.
*Apex*.—Round.
*Base*.—Pointed.
*Margin*.—Straight.
*Color*.—RHS Green 139B.
Peduncles: None.
Fragrance: Soft floral scent.

REPRODUCTIVE ORGANS

Androecium:
Stamens:
*Number*.—50.
Anthers:
*Shape*.—Elongated, narrow.
*Length*.—About 0.05 cm.
*Color*.—RHS Yellow 15A.
*Pollen*.—Color: RHS Yellow 15A.
Gynoecium:
Pistil:
*Number*.—50.
*Length*.—0.4 cm.
*Style*.—Shape: V-shaped. Length: 1 cm. Color: RHS Yellow 9C.
*Stigma*.—Shape: V-shaped. Color: RHS Yellow 9C. Ovary Color: RHS Yellow 9C.

OTHER CHARACTERISTICS

Seeds and fruits: Not observed.
Disease/pest resistance: Neither resistance nor susceptibility to typical *Dahlia* pests and diseases observed.
Temperature tolerance: Tolerant from 1° to 38° C.

What is claimed is:

1. A new and distinct cultivar of *Dahlia* plant named 'DDAHCHPRPL' as herein illustrated and described.

* * * * *